United States Patent [19]

Crooks

[11] Patent Number: 4,572,915
[45] Date of Patent: Feb. 25, 1986

[54] CLEAR MICELLIZED SOLUTIONS OF FAT SOLUBLE ESSENTIAL NUTRIENTS

[75] Inventor: Michael J. Crooks, Chatswood, Australia

[73] Assignees: Bioglan Laboratories; Bioglan, Inc., both of Santa Ana, Calif.

[21] Appl. No.: 605,797

[22] Filed: May 1, 1984

[51] Int. Cl.⁴ .................. A61K 31/59; A61K 31/20; A61K 31/045; A61K 31/355

[52] U.S. Cl. .................. 514/458; 424/195.1; 514/167; 514/168; 514/546; 514/552; 514/558; 514/725; 514/904

[58] Field of Search ............ 424/284, 237; 514/167, 514/168, 458, 546, 552, 558, 725, 904

[56] References Cited

U.S. PATENT DOCUMENTS

| | | | |
|---|---|---|---|
| 3,900,561 | 8/1975 | Davis et al. | 424/243 |
| 4,075,333 | 2/1978 | Josse | 424/284 |
| 4,201,235 | 5/1980 | Ciavatta | 424/284 |

OTHER PUBLICATIONS

McCutcheon's–Detergent & Emulsifiers–1971 Annual–Emulphor EL.
Chem. Abst., 84:126779(p) (1976)–Joachim.
Chem. Abst., 85:72466(j) (1976)–Kettler et al.
Chem. Abst., 85:166640(p) (1976)–Josse.
Chem. Abst., 100:39628(n) (1984)–Richter et al.

Primary Examiner—Douglas W. Robinson
Attorney, Agent, or Firm—Klein & Szekeres

[57] ABSTRACT

Micellized aqueous formulations for fat soluble vitamins, essential nutrients, herb oils and pharmaceutical agents are obtained by a process wherein the fat soluble vitamin, essential nutrient or agent is first admixed with a suitable amount of polyethoxylated castor oil and a pharmaceutically acceptable polyol, such as glycerol to provide a non-aqueous phase. Thereafter, an aqueous phase containing mostly water and optionally a preservative, such as sodium benzoate, is slowly added to the agitated non-aqueous phase in such a manner that the temperature of the non-aqueous phase, including the aqueous phase added thereto, is maintained at an elevated temperature, preferably between approximately 60° to 100° C. After cooling, the final admixture is clear, homogeneous, having micelles of approximately 2 microns or smaller size. Human subjects exhibit significantly higher blood plasma levels of vitamins A and E after ingestion of the formulation of the present invention, then after ingestion of comparable doses of prior art vitamin A and E formulations.

42 Claims, No Drawings

CLEAR MICELLIZED SOLUTIONS OF FAT SOLUBLE ESSENTIAL NUTRIENTS

BACKGROUND OF INVENTION

1. Field of the Invention

The present invention is directed to a formulation for drugs, vitamins and essential nutrients. More particularly, the present invention is directed to substantially clear aqueous formulations for fat soluble essential nutrients which remain clear when added to water or beverages for human consumption, and which permit enhanced absorption of the essential nutrients from the digestive system.

2. Brief Description of the Prior Art

Formulations of fat soluble vitamins and essential nutrients used as nutritional supplements in human and animal health care and maintenance, are well known in the art.

To be acceptable as nutritional supplements intended for human consumption, such formulations must be reasonably palatable. In addition they must also permit, and preferably facilitate, absorption of the fat soluble vitamins or essential nutrients from the digestive system.

The simplest formulations of fat soluble essential nutrients merely contain the nutrients in an edible oil carrier medium. A disadvantage of these formulations is their low palatability, and relatively poor absorption of the nutrient in the human digestive system.

Fat soluble vitamins, such as vitamin A, D, and E, and fat soluble essential nutrients and the like, such as essential fatty acids and beta carotene, have also been provided in the prior art in an aqueous carrier medium. These formulations of the prior art are, however, turbid, because they either contain water insoluble droplets of an oil phase, or micelles of too large size to permit substantial optical homogeneity.

It will be readily appreciated by those skilled in the art, that a turbid, or non-homogeneous nutrional supplement is less desirable from the viewpoint of the consumer than a clear solution. Therefore, the food supplements, vitamins and related industry has been striving for a long time to create substantially clear, substantially homogeneous aqueous formulations for fat soluble vitamins and other essential nutrients. In addition, the food supplements, vitamins, and related industry has been striving for a long time to provide formulations which have improved absorption characteristics in the human digestive system. The present invention satisfies both of these long sought after goals of the prior art.

SUMMARY OF THE INVENTION

It is an object of the present invention to provide aqueous formulations for fat soluble vitamins, essential nutrients, non-water soluble drugs, medicinal and pharmaceutical agents, and the like, which are substantially clear, homogeneous, and cause no turbidity when added to an aqueous beverage prior to ingestion.

It is another object of the present invention to provide formulations for fat soluble vitamins, essential nutrients, non-water soluble drugs, medicinal and pharmaceutical agents and the like, which permit enhanced absorption of the vitamin, nutrient, drug or agent from the digestive tract.

The foregoing and other objects and advantages are attained by formulations of one or more fat soluble vitamins, essential nutrients or drugs, wherein the vitamin, nutrient or drug is dispersed in an aqueous carrier in micelles of approximately 2 microns or smaller.

The formulations or compositions of the invention are obtained by admixing polyethoxylated caster oil with the fat soluble vitamin, essential nutrient or drug, together with a pharmaceutically acceptable water miscible polyol, to obtain a non-aqueous phase.

The non-aqueous phase is heated to at least 60° C., and an aqueous phase comprising predominently water and optionally a preservative is slowly added while the admixture is agitated and kept at a temperature of at least 60° C. The resulting mixture is cooled, and thereafter optionally diluted with aqueous diluents and flavoring agents.

Alternatively, heat sensitive fat soluble essential vitamins, nutrients, drugs or related pharmaceutical agents such as beta-carotene, or herb oils (such as odorless garlic oil containing scordinin) are mixed with polyethoxylated castor oil and a pharmaceutically acceptable polyol or a flavoring agent such as lemon spirit, or both, to provide a substantially clear micellized solution.

The features of the present invention can be best understood, together with further objects and advantages by reference to the following description.

BRIEF DESCRIPTION OF THE PREFERRED EMBODIMENTS, AND SPECIFIC EXAMPLES

The following specification sets forth the preferred embodiments of the present invention. The embodiments and examples set forth herein are the best modes contemplated by the inventor for carrying out his invention in a commercial environment, although it should be understood that various modifications can be accomplished within the parameters of the present invention.

In accordance with the present invention, aqueous formulations or solutions of one or more fat soluble vitamins, essential nutrients, or fat soluble drugs, medicinal or pharmaceutical agents, are obtained. The aqueous formulations or solutions are substantially clear and homogeneous, in the sense that they are not turbid, and contain no droplets of non-aqueous oily phase, or solid particulates.

Fat soluble vitamins which can be solubilized in accordance with the present invention include d-alpha-tocopherol (vitamin E) and its pharmaceutically acceptable derivatives having vitamin E activity, such as d-alpha-tocopheryl acetate, other esters of d-alpha tocopherol, retinol (vitamin A) and its pharmaceutically acceptable derivatives having vitamin A activity, such as the palmitate and other esters of retinol, and calciferol (vitamin D) and its pharmaceutically acceptable derivatives or precursors having vitamin D activity.

Other fat soluble essential nutrients which may be solubilized in an aqueous carrier in accordance with the present invention include essential fatty acids such as cis linoleic acid, alpha and gamma linolenic acids, certain esters of the essential fatty acids where the esterifying alcohol has a short alkyl carbon chain, such as ethyl linoleate, as well as pharmaceutically acceptable natural sources for the essential fatty acids, such as evening primrose oil, fish oil and safflower oil.

Beta carotene, and certain herb oils such as garlic oil containing scordinin are other examples of important fat soluble nutritional supplements which can be solubilized in accordance with the present invention. The above-mentioned examples of fat soluble vitamins, essential nutrients, drugs and related pharmaceutically active compounds are hereinafter jointly referred to, in the generic sense, as fat soluble essential nutrients.

Thus, it has been discovered in accordance with the present invention, that substantially clear, substantially homogeneous solutions of fat soluble essential nutrients, or fat soluble medicinal agents, can be obtained in a process where a suitable non-aqueous phase including the fat soluble essential nutrient is prepared, and is thereafter slowly admixed at an elevated temperature with an aqueous diluent.

More particularly, in the process, one or more fat soluble essential nutrients is admixed with a pharmaceutically acceptable emulsifying agent, such as polyethoxylated castor oil, and also with a pharmaceutically acceptable water miscible polyol, such as glycerol or diethylene glycol. The mixture of the fat soluble essential nutrient, polyethoxylated castor oil, and polyol, preferably glycerol, usually forms a homogeneous non-aqueous phase already at room temperature, or becomes homogeneous upon heating to approximately 60° C. or higher temperature.

Approximately 2 to 6 units of weight of polyethoxylated castor oil and approximately 1 to 2 units of weight of glycerol are used for each unit of weight of the essential nutrient to prepare the non-aqueous phase. For the preparation of the novel formulation of the present invention, the non-aqueous phase is then heated to at least 55° C., preferably to approximately 60° C., and most preferably to 85° to 90° C.

As an important feature of the process of the present invention, an aqueous phase is slowly added to the continuously agitated non-aqueous phase in such a manner that the temperature of the admixed non-aqueous and aqueous phases is maintained at an elevated level. The foregoing is best accomplished when the aqueous phase, to be slowly added to the agitated non-aqueous phase, is itself heated and maintained at an elevated temperature. Preferably, the aqueous phase is heated to approximately 60° to 80° C., and is kept in that temperature range while it is slowly added to the non-aqueous phase. Best results are usually obtained when the non-aqueous phase is agitated and heated to maintain a temperature of approximately 80° to 100° C. while the aqueous phase is added thereto.

Addition of the aqueous phase to the non-aqueous phase is a relatively slow process. In accordance with the present invention, the aqueous phase typically comprises predominantly water, having a relatively small amount of a dissolved pharmaceutically acceptable preservative, such as sodium benzoate. For each unit of weight of the non-aqueous phase, typically and approximately 0.8 to 1.5 unit of weight of the aqueous phase is added during this step. Yet, the addition usually requires approximately one hour, or still longer time periods.

The aqueous phase, which is added in the above-described step to the non-aqueous phase, may also contain flavoring agents and alcohols such as ethyl alcohol.

After the above-described addition step is completed, the mixture is further agitated slowly to minimize aeration, and is cooled to 35° C. or lower temperature. The compositions or formulations, prepared in accordance with the present invention, consist of a single, clear, homogeneous phase by the time the temperature reaches 35° C. in the cooling step. For most compositions prepared in accordance with the present invention, the cooling is performed slowly. For example a formulation of d-alpha tocopheryl acetate (described in detail as Example 1) is cooled from approximately 60° to 30° C. in approximately 3 hours.

The formulations and compositions of the present invention may optionally include further diluents, such as water, aqueous alcohol solutions, and flavoring agents. In addition, the pH of the composition may be adjusted with suitable, pharmaceutically acceptable acids (such as citric acid) or buffering agents. The diluent, such as water, and the acid or buffering agent are preferably added to the composition after the cooling step, at 30° C. or lower temperature.

In the case of certain specific examples, it is important to add the diluent and the buffering agent after the cooling step, otherwise the formulation remains, or becomes turbid.

In the case of certain formulations or compositions prepared in accordance with the present invention, the cooling step must be conducted rapidly, as for example in the preparation of a formulation for essential fatty acids. (Example 5)

Moreover, certain temperature sensitive fat soluble essential nutrients or nutritional supplements such as beta-carotene and garlic oil (which has a temperature sensitive active ingredient scordinin) maybe formulated in accordance with the present invention. In these cases, heating of the admixture of beta-carotene with polyethoxylated castor oil is avoided altogether. Rather, the admixture is agitated with minimum exposure to atmospheric oxygen, for a relatively long period of time. Thereafter, an aqueous alcoholic extract of a flavoring agent, such as lemon spirit U.S.P., or a polyol, or both are added to provide a substantially clear, (slightly opaque) solution.

The polyethoxylated castor oil, which is used as the emulsifying agent in accordance with the present invention, is commercially available, for example, from BASF Aktiengesellschaft, Ludwigshafen, West Germany) under the tradename CREMOPHOR EL, and from GAF Corporation (N.Y.) under the tradename EMULPHOR EL. In certain formulations prepared in accordance with the present invention, use of one or the other of the above-mentioned commercial product provides better results. This is indicated in the below-given specific examples.

Certain technical specification of CREMOPHOR EL, and EMULPHOR EL, are recited herein in Table 1a and 1b, respectively.

TABLE 1a

| CREMOPHOR EL - PROPERTIES | |
|---|---|
| Viscosity (Hoppler) at 25° | 700-850 cP |
| Density at 25° | 1.05-1.06 g/ml |
| Refractive index at 25° C. | approx. 1.471 |
| Saponification value, DIN 53401 | 65-70 |
| Hydroxyl value, DGF E-III 3c (55) | 65-78 |
| Iodine value (Kaufman) | 28-32 |
| Acid value | [2 |
| Water content (K. Fischer) | [3% |
| pH value of 10% aqueous solution | 6-8 |

TABLE 1b

| EMULPHOR | EL-620 | EL-719 |
|---|---|---|
| Chemical Composition | polyoxyethylated castor oil | polyoxyethylated castor oil |
| CTFA Name | PEG-30 castor oil | PEG-40 castor oil |
| Active-Ingredient Content | 100% (essentially) | 96% minimum |
| Moisture Content | 0.5% | 3.5% |

TABLE 1b-continued

| EMULPHOR | EL-620 | EL-719 |
|---|---|---|
| (typical) Physical Form | | |
| 0° C. | opaque, tan, very viscous liquid | pale-white, waxy solid |
| 25° C. | clear, light-brown liquid | clear yellow liquid |
| 100° C. | same description as at 25° C., but with reduced viscosity | clear yellow liquid |
| Appearance of 10% aqueous soln (25° C.) | clear | clear |
| Color | yellow to light-brown | greenish-yellow to light-amber |
| Varnish Color Scale | 5 maximum | 4 maximum |
| Odor | mild oily | oily |
| Viscosity (25° C.) | 600–1,000 cps | 500–800 cps |
| Specific Gravity (25° C.) | 1.04–1.05 | 1.06–1.07 |
| Density (25° C.) | 8.7–8.8 lb/gal | 8.9–9.0 lb/gal |
| Flash Point (ASTM method) | 291–295° C. | 275–279° C. |
| Fire Point (ASTM method) | 322–326° C. | 328–332° C. |

Table 2 shows certain weight ratios of components in specific examples of the compositions or formulations prepared in accordance with the present invention.

TABLE 2

| SPECIFIC EXAMPLE | Essential nutrient/ active ingredient | Emulsifier active ingredient | Glycerol active ingredient | Aqueous Phase non-aqueous phase | Vitamin activity, or concentration of final formulation |
|---|---|---|---|---|---|
| 1 | d-alpha tocopheryl-acetate | 2.16 | 1.3 | 0.935 | 150–160 I.U./ml |
| 2 | palmitate ester of retinol | 3.86 | 2.32 | 1.04 | 105,000–120,000 I.U./ml |
| 3 | d-alpha tocopheryl acetate and palmitate ester of retinol | 3.185 | 1.92 | 1.01 | 100–107 I.U./ml (E), and 2100–2550 I.U./ml (A). |
| 4 | d-alpha tocopherol; palmitate ester of vitamin A | 6.05 | 3.63 | 1.071 | |
| 5 | evening primrose oil | 3.0 | 1.2 | 0.87 | 10% essential fatty acid (by weight) |

In addition to flavoring agents, water soluble vitamins and essential nutrients, such as thiamine hydrochloride, riboflavin-5-phosphate, niacinamide, d-panthenol, ascorbic acid, pyridoxine hydrocholoride, cyanocobalamin, folic acid, and d-biotin, can also be included in the formulations or compositions of the present invention. Thus, the present invention renders it possible to provide one or more fat soluble and virtually all water soluble vitamins in a single, palatable, optically clear, aqueous formulation.

The fat soluble essential nutrients are solubilized in accordance with the present invention in micelles of approximately 2 microns or smaller size. Upper concentration limits of the fat soluble vitamins and essential nutrients are imposed by the requirement that the final preparation must not be turbid. Therefore, the upper limit for vitamin E activity of a formulation prepared in accordance with the present invention from alpha-tocopheryl acetate, is approximately 200 International Units (I.U.) per mililiter of the formulation. The upper limit of vitamin A activity (from retinyl palmitate) is approximately 140,000 I.U. per mililiter of formulation. Upper limits of vitamin E and vitamin A activity in a formulation containing both of these fat soluble vitamins, of course, depend on the ratio of the individual ingredients.

Experience has shown that the formulations of the present invention are chemically stable, and remain optically clear and homogeneous for a prolonged period of time, without significant loss of fat soluble vitamin activity.

Perhaps most importantly, however, from the standpoint of human and animal health care, experiments have demonstrated significantly enhanced uptake of vitamins E and A in normal human subjects from the formulations of the present invention, when compared to prior art "emulsified" and "oil based" vitamin E and A formulations.

More specifically, Table 3 shows human blood plasma vitamin E level increases over base level (in micromols per mililiter of plasma) four (4), eight (8) and twenty-four (24) hours after ingestion of 500 I.U. of vitamin E by normal human subjects, in a prior art oil based formulation, in a prior art emulsified formulation, and in the formulation of the present invention, respectively. Table 3 reveals that the formulation of the present invention provides, 4, 8 and 24 hours after ingestion 2.2, 1.9 and 2.7 times higher blood plasma vitamin E levels, respectively, than the prior art emulsified formulation.

Table 4 shows in a fashion similar to Table 3, blood plasma vitamin A levels in normal human subjects, four (4) and eight (8) hours after oral ingestion of 50,000 I.U. of vitamin A, in prior art "oil based" formulations, in prior art emulsified formulations, and in the formulation of the present invention. Table 4 reveals, that 4 and 8 hours after ingestion of the formulation of the present invention the blood plasma vitamin A levels are 2.1 and 2.4 times higher, respectively, than after ingestion of prior art emulsified formulations.

As it will be readily appreciated by those skilled in the art, enhanced blood plasma levels of these important fat soluble nutrients is probably due to increased or enhanced absorption of the nutrient from the digestive tract.

The herein-below given specific examples of formulations of the present invention should be considered exemplary rather than limiting in nature. The scope of the present invention should be construed solely from the appended claims read in light of the present specifications and description.

TABLE 3

| | Blood Plasma Vitamin E Level Increase Over Base Line (micromols per mililiter) | | |
|---|---|---|---|
| | Prior art oil based formulation | Prior Art emulsified formulation | Present invention |
| 4 hours after oral dose of 500 I.U. | 2.5 | 5.5 | 12.0 |
| 8 hours after oral dose of 500 I.U. | 4.5 | 8.2 | 16.0 |
| 12 hours after oral dose of | 2.5 | 4.5 | 12.5 |

TABLE 3-continued

| Blood Plasma Vitamin E Level Increase Over Base Line (micromols per mililiter) | | |
| --- | --- | --- |
| Prior art oil based formulation | Prior Art emulsified formulation | Present invention |
| 500 I.U. | | |

TABLE 4

| Blood Plasma Vitamin A Level Increase Over Base Line (micromols per mililiter) | | | | | |
| --- | --- | --- | --- | --- | --- |
| 4 hours after oral dose of 50,000 I.U. | | | 8 hours after oral dose of 50,000 I.U. | | |
| prior art oil based formulation | prior art emulsified formulation | present invention | prior art "oil" formulation | prior art emulsified formulation | present invention |
| 0.2 | 0.5 | 1.075 | 0.10 | 0.20 | 0.475 |

SPECIFIC EXAMPLES

EXAMPLE 1

Vitamin E Formulation 11.58 Kg of d-alpha-tocopheryl acetate U.S.P., 25 Kg of polyethoxylated castor oil [CREMOPHOR EL (BASF)] and 15 Kg of glycerol U.S.P. are mixed in a stainless steel tank, and then heated to approximately 85°–90° C. to provide a homogeneous non-aqueous phase.

0.25 Kg of sodium benzoate is dissolved in 48 liters of deionized water in a tank, and the solution is heated to approximately 65° C. to provide an aqueous phase.

The heated aqueous phase is slowly added (in about one hour) to the agitated non-aqueous phase, while the agitated phase is maintained at 85°–90° C. Agitation is continued with an effort to minimize aeration while the mixture is slowly cooled from 60° to 30° C. in about 3 hours. The solution becomes clear during cooling.

At about 30° C., the pH of the solution is adjusted to pH 5 by addition of citric acid (50% aqueous solution). At about 20°–25° C., deionized water is added to provide a final volume of 100 liters. The pH of the final product is 4.8–5.2; vitamin E activity is 150–160 I.U./ml.

EXAMPLE 2

Vitamin A Formulation

The procedure given in Example 1 is followed with 6.47 kg of the palmitate ester of retinol. The pH of the solution is adjusted to 6.5 with citric acid. Activity of the final product is 105,000 to 120,000 I.U./ml.

EXAMPLE 3

Combined Vitamins A and E Formulations

The procedure given in Example 1 is followed with 7.72 kg of d-alpha-tocopheryl acetate and 130 g of the retinyl palmitate. The pH is adjusted to 4.8–5.2. The final product has 100–107.5 I.U./ml of vitamin E activity and 2100–2500 I.U./ml vitamin A activity.

EXAMPLE 4

Combined Vitamin A, E and Water Soluble Vitamins Formulation 1.3 g of retinyl palmitate, 40 g of d-alpha-tocopherol, 250 g of polyethoxylated castor oil [CREMOPHOR EL (BASF)] and 150 g of glycerol are mixed and heated to 80° C. or higher temperature, to provide a non-aqueous phase.

A solution of 2.5 sodium benzoate in 470 g of deionized water is heated to 65° C., and is slowly added to the non-aqueous phase, while the non-aqueous phase is agitated and maintained at approximately 80° C.

Thereafter the solution is cooled slowly to 35° C., at which time the following are added as solids until dissolved:

| | |
| --- | --- |
| 2.2 g | thiamine hydrochloride |
| 0.5 g | riboflavin-5-phosphate |
| 12.0 g | niacinamide |
| 10.0 g | d-panthenol |
| 40.0 g | ascorbic acid |
| 2.0 g | pyridoxine hydrochloride |
| 0.01 g | cyanocobalamin |
| 0.05 g | folic acid |
| 0.10 g | d-biotin |
| 20 g | lemon spirit U.S.P. (or other flavoring agent) |

EXAMPLE 5

Essential Fatty Acid Formulation

In a procedure similar to the procedure described in connection with Example 1, 100 g of evening primrose oil, 300 g of polyethoxylated castor oil, and 120 g of glycerol are mixed at 65° C. until a clear solution (non-aqueous phase) is obtained.

A heated (65° C.) solution of 2.5 g of sodium benzoate in 490 g of deionized water is slowly added to the non-aqueous phase, while the non-aqueous phase is maintained at 65° and is agitated.

After 15 more minutes of agitation, the admixture is cooled quickly to ambient temperature by adding 350 g of ice (made of deionized water). Citric acid (approximately 1.25 g) is then added to adjust the pH to 5.0, followed by 20 g of lemon spirit U.S.P. The final product contains 10% (by weight) essential fatty acids. The same procedure may be used with safflower oil, fish oil, and other natural oil sources for essential fatty acids.

EXAMPLE 6

Beta-carotene Formulation

Beta-carotene [20% suspension in peanut oil, (Roche) particle size 10 microns or smaller] is mixed with polyethoxylated castor oil [EMULPHOR EL (GAF)] in weight ratio of 1 to 7 (suspension to EMULPHOR). The mixture is agitated at room temperature, overnight, with minimum exposure to atmospheric oxygen. Thereafter, lemon spirit U.S.P. is added in sufficient quantity to provide 20% (by weight) of the final product, which contains about 20 mg (33,000 I.U.) of beta-carotene per mililiter.

EXAMPLE 7

Garlic Oil Formulation

Odorless garlic oil (containing scordinin) is mixed with polyethoxylated castor oil [EMULPHOR EL (GAF)] in weight ratio of 1 to 2. Thereafter, sufficient polyethylene glycol, (molecular weight approximately 400) is added to provide a substantially clear final product which contains 250 mg of garlic oil per mililiter.

What is claimed is:

1. A substantially clear micellized aqueous solution of one or more fat soluble essential nutrients selected from a group consisting of essential fatty acids, alpha-tocopherol, pharmaceutically acceptable esters of alpha-tocopherol having Vitamin E activity, retinol, pharmaceutically acceptable esters of retinol having Vitamin A activity, calciferol and pharmaceutically acceptable derivatives of calciferol having vitamin D activity, said micellized aqueous solution having been prepared by a process comprising the steps of:

mixing one or more of the fat soluble essential nutrients with an emulsifying agent comprising polyethoxylated castor oil, and with a water miscible pharmaceutically acceptable polyol to obtain a first non-aqueous phase in ratios of approximately 2 to 6 units of weight of emulsifying agent and approximately 1 to 2 units of weight of polyol are used for each unit of weight of the fat soluble essential nutrients;

slowly adding approximately 0.8 to 1.5 unit of weight for each unit of weight of said non-aqueous phase of a warm aqueous phase consisting essentially of water while stirring the non-aqueous phase, rate of addition of the warm aqueous phase to the non-aqueous phase being such that the admixture of the two phases is at least at 55° C. substantially during the entire step of addition, and after adding the aqueous phase to the non-aqueous phase, cooling the resulting clear admixture to at least 35° C.

2. The composition of claim 1 prepared by the process further comprising the step of heating the non-aqueous phase to approximately 60° to 100° C., and keeping the non-aqueous phase in said temperature range substantially during the entire step of adding the aqueous phase.

3. The composition of claim 1 prepared by the process wherein after adding the aqueous phase to the non-aqueous phase, the step of cooling is conducted at the rate of reducing the temparature of the composition from approximately 60° C. to approximately 30° C. in approximately 3 hours.

4. The composition of claim 1 prepared by the process wherein during addition of the warm aqueous phase to the non-aqueous phase, the temperature of the aqueous phase is maintained at approximately 60° C. to 80° C.

5. The composition of claim 1 prepared by the process further comprising the step of adding an aqueous diluent to the cooled admixture.

6. The composition of claim 1 wherein the water miscible polyol is selected from a group consisting of glycerol and 1,2-diethylene glycol.

7. The composition of claim 6 wherein the polyol is glycerol.

8. The composition of claim 1 wherein the essential nutrient is d-alpha-tocopheryl acetate.

9. The composition of claim 8 containing approximately 100 to 200 International Units of Vitamin E activity per mililiter of composition.

10. The composition of claim 1 wherein the essential nutrient is the palmitate ester of retinol.

11. The composition of claim 10 containing approximately 50,000 to 130,000 International Units of Vitamin A activity per mililiter of composition.

12. The composition of claim 1 containing approximately 50 to 150 International Units of vitamin E activity and 1500-to 2800 International Units of vitamin A activity per mililiter of the composition.

13. The composition of claim 1 wherein the essential nutrients are approximately 50 to 150 International Units of d-alpha-tocopherol and 1500 to 2800 International Units of the palmitate ester of retinol per milliliter of composition.

14. The composition of claim 1 wherein the essential nutrients are essential fatty acids, and wherein one or more sources for the essential fatty acids, selected from a group consisting of evening primrose oil, safflower oil and fish oil, are mixed with the polyol in the mixing step.

15. The composition of claim 1 containing approximately 5 to 20 percent by weight, of essential fatty acid.

16. An optically substantially clear, substantially homogeneous micellized aqueous solution of one or more fat soluble essential nutrients, having micels of the size not substantially exceeding 2 microns, which solution remains substantially clear when added to an aqueous diluent such as a beverage for human consumption, the fat soluble essential nutrient being selected from a group consisting of essential fatty acids, alpha-tocopherol, pharmaceutically acceptable derivatives of alpha-tocopherol having Vitamin E activity, retinol, pharmaceutically acceptable derivatives of retinol having Vitamin A activity, calciferol and pharmaceutically acceptable derivatives of calciferol having vitamin D activity, said composition having been prepared by a process comprising the steps of:

mixing one or more of the fat soluble nutrients with polyethoxylated castor oil, and with a water soluble pharmaceutically acceptable polyol in ratios wherein approximately 2.0 to 6.0 unit of weight of polyethoxylated castor oil and approximately one (1) to two (2) unit of weight of polyol is added for each unit of weight of fat soluble essential nutrient;

heating the mixture of the one or more fat soluble essential nutrients, of the polyethoxylated castor oil and of the polyol to at least 60° C. to obtain a substantially homogeneous non-aqueous phase;

slowly adding to the non-aqueous phase an aqueous phase consisting essentially of water, while agitating the non-aqueous phase, and maintaining the same, including the aqueous phase slowly added thereto, at a temperature of at least 60° C., the quantity of the aqueous phase added to the non-aqueous phase being approximately 0.8 to 1.5 units of weight for each unit of weight of the non-aqueous phase, and cooling the admixture of the aqueous and non-aqueous phases to at least 35° C.

17. The composition of claim 16 wherein the process of preparing the composition further includes after the step of cooling a step of diluting the substantially clear, substantially homogeneous admixed aqueous and non-aqueous phases with a diluent comprising water.

18. The composition of claim 16 wherein the fat soluble essential nutrients are added to the composition in the form of sources selected from a group consisting of evening primrose oil, safflower oil, and fish oil, and wherein in the process for preparing the composition the step of cooling is conducted as rapid cooling.

19. The composition of claim 18 wherein in the process for preparing the composition, the step of rapid cooling is conducted by rapidly adding ice to the admixture of aqueous and non-aqueous phases.

20. The composition of claim 16 wherein in the process for preparing the composition the step of heating comprises heating to at least 80° C.

21. The composition of claim 20 wherein in the process for preparing the composition, during the step of slowly adding the aqueous phase to the non-aqueous phase the aqueous phase being added is approximately at 60° C. or higher temperature.

22. The composition of claim 21 further comprising an effective amount of a pharmaceutically acceptable preservative, such as sodium benzoate.

23. The composition of claim 22 further comprising a flavoring agent such as lemon spirit.

24. A substantially optically clear, substantially homogeneous aqueous micellized solution of one or more fat soluble essential nutrients, micel size of the nutrients being of approximately two (2) microns or smaller, the solution being capable of remaining substantially homogeneous and substantially optically clear when added to a substantially clear substantially homogeneous, substantially clear aqueous phase such as water or a beverage for human consumption, the essential nutrient being selected from a group consisting of essential fatty acids, alpha-tocopherol, pharmaceutically acceptable derivatives of alpha-tocopherol having Vitamin E activity, retinol, pharmaceutically acceptable derivatives of retinol having Vitamin A activity, calciferol and pharmaceutically acceptable derivatives of calciferol having vitamin D activity, the solution essentially consisting of:
one or more of the essential nutrients as defined above;
a pharmaceutically acceptable polyol in an amount which is approximately 1 to 2 units of weight for each unit of weight of the fat soluble essential nutrients;
polyethoxylated castor oil, in an amount which is approximately 2 to 6 units of weight for each unit of weight of the fat soluble essential nutrients, and
water in an amount which is approximately 0.8 to 1.5 units of weight for each unit of weight of the combined weight of the fat soluble essential nutrients, of the polyol and of the polyethoxylated castor oil.

25. The composition of claim 24 further comprising a flavoring agent.

26. The composition of claim 24 wherein the fat soluble essential nutrient is d-alpha-tocopheryl acetate and wherein the composition contains approximately 100 to 200 International Units of vitamin E activity per milliliter of the composition.

27. The composition of claim 24 wherein the fat soluble essential nutrient is a derivative of retinol and wherein the composition contains approximately 50,000 to 130,000 International Units of vitamin A activity per milliliter of composition.

28. The composition of claim 24 wherein the fat soluble essential nutrients are d-alpha-tocopherol acetate and a derivative of retinol, and wherein the composition contains approximately 50 to 150 International Units of vitamin E activity, and 1500 to 2800 International Units of vitamin A activity per milliliter of composition.

29. The composition of claim 24 wherein the fat soluble essential nutrients are d-alpha-tocopherol and a derivative retinol, and wherein the composition further comprises at least one water soluble essential nutrient.

30. The composition of claim 24 wherein the fat soluble essential nutrient is derived from a group selected from evening primrose oil, safflower oil and fish oil.

31. A process for preparing a substantially clear micellized aqueous solution of one or more fat soluble essential nutrients selected from a group consisting of essential fatty acids, alpha-tocopherol, pharmaceutically acceptable esters of alpha-tocopherol having Vitamin E activity, retinol, pharmaceutically acceptable esters of retinol having Vitamin A activity, calciferol and pharmaceutically acceptable derivatives of calciferol having vitamin D activity, the process comprising the steps of:
mixing one or more of the fat soluble essential nutrients with an emulsifying agent comprising polyethoxylated castor oil, and with a water miscible pharmaceutically acceptable polyol to obtain a first non-aqueous phase in ratios of approximately 2 to 6 units of weight of emulsifying agent and approximately 1 to 2 units of weight of polyol are used for each unit of weight of the fat soluble essential nutrients;
slowly adding approximately 0.8 to 1.5 unit of weight for each unit of weight of said non-aqueous phase of a warm aqueous phase consisting essentially of water while stirring the non-aqueous phase, rate of addition of the warm aqueous phase to the non-aqueous phase being such that the admixture of the two phases is at least at 55° C. substantially during the entire step of addition, and
after adding the aqueous phase to the non-aqueous phase, cooling the resulting clear admixture to at least 35° C.

32. The process of claim 31 further comprising the step of heating the non-aqueous phase to approximately 60° to 100° C., and keeping the non-aqueous phase in said temperature range substantially during the entire step of adding the aqueous phase.

33. The process of claim 31 wherein after adding the aqueous phase to the non-aqueous phase, the step of cooling is conducted at the rate of reducing the temperature of the composition from approximately 60° C. to approximately 30° C. in approximately 3 hours.

34. The process of claim 31 wherein during addition of the warm aqueous phase to the non-aqueous phase, the temperature of the aqueous phase is maintained at approximately 60° to 80° C.

35. The process of claim 31 further comprising the step of adding an aqueous diluent to the cooled admixture.

36. The process of claim 31 wherein the water miscible polyol is selected from a group consisting of glycerol and 1,2-diethylene glycol.

37. A process for preparing an optically substantially clear, substantially homogeneous micellized aqueous solution of one or more fat soluble essential nutrients, having micels of the size not substantially exceeding 2 microns, which solution remains substantially clear when added to an aqueous diluent such as a beverage for human consumption, the fat soluble essential nutrient being selected from a group consisting of essential fatty acids, alpha-tocopherol, pharmaceutically acceptable derivatives of alpha-tocopherol having Vitamin E activity, retinol, pharmaceutically acceptable derivatives of retinol having Vitamin A activity, calciferol and pharmaceutically acceptable derivatives of calciferol having vitamin D activity, said process comprising the steps of:
mixing one or more of the fat soluble nutrients with polyethoxylated castor oil, and with a water soluble pharmaceutically acceptable polyol in ratios wherein approximately 2.0 to 6.0 unit of weight of polyethoxylated castor oil and approximately one (1) to two (2) unit of weight of polyol is added for each unit of weight of fat soluble essential nutrient;

heating the mixture of the one or more fat soluble essential nutrients, of the polyethoxylated castor oil and of the polyol to at least 60° C. to obtain a substantially homogeneous non-aqueous phase;

slowly adding to the non-aqueous phase an aqueous phase consisting essentially of water, while agitating the non-aqueous phase, and maintaining the same, including the aqueous phase slowly added thereto, at a temperature of at least 60° C., the quantity of the aqueous phase added to the non-aqueous phase being approximately 0.8 to 1.5 units of weight for each unit of weight of the non-aqueous phase, and cooling the admixture of the aqueous and non-aqueous phases to at least 35° C.

38. The process of claim 37 further including a step of diluting the substantially clear, substantially homogeneous admixed aqueous and non-aqueous phases with a diluent comprising water.

39. The process of claim 37 wherein in the step of mixing the fat soluble essential nutrients are contained in sources selected from a group consisting of evening primrose oil, safflower oil, and fish oil, and wherein the step of cooling is conducted as rapid cooling.

40. The process of claim 39 wherein the step of rapid cooling is conducted by rapidly adding ice to the admixture of aqueous and non-aqueous phases.

41. The process of claim 37 wherein the step of heating comprises heating to at least 80° C.

42. The process of claim 41 wherein during the step of slowly adding the aqueous phase to the non-aqueous phase the aqueous phase being added is approximately at 60° C. or higher temperature.

* * * * *